(12) United States Patent
Reggiano

(10) Patent No.: US 11,471,577 B2
(45) Date of Patent: Oct. 18, 2022

(54) SYSTEM FOR PROVIDING AN INTEGRATED ARTERIAL FILTER INTO AN OXYGENATOR, MINIMIZING ADDED PRIMING VOLUME

(71) Applicant: Sorin Group Italia S.r.l., Milan (IT)

(72) Inventor: Stefano Reggiano, Medolla (IT)

(73) Assignee: Sorin Group S.r.l., Milan (IT)

( * ) Notice: Subject to any disclaimer, the term of this patent is extended or adjusted under 35 U.S.C. 154(b) by 536 days.

(21) Appl. No.: 16/439,019

(22) Filed: Jun. 12, 2019

(65) Prior Publication Data

US 2019/0290821 A1  Sep. 26, 2019

Related U.S. Application Data

(63) Continuation of application No. 15/121,768, filed as application No. PCT/IT2014/000058 on Feb. 28, 2014, now Pat. No. 10,369,262.

(51) Int. Cl.
*A61M 1/16* (2006.01)
*B01D 63/10* (2006.01)

(52) U.S. Cl.
CPC ........... *A61M 1/1698* (2013.01); *B01D 63/10* (2013.01); *A61M 2205/7536* (2013.01); *B01D 2313/38* (2013.01)

(58) Field of Classification Search
CPC .............. A61M 1/1698; A61M 1/3627; A61M 2205/7536; A61M 2205/7545; B01D 63/10; B01D 63/02; B01D 2313/38; B01D 2313/23

See application file for complete search history.

(56) References Cited

U.S. PATENT DOCUMENTS

| | | | |
|---|---|---|---|
| 3,339,341 A | | 9/1967 | Murdock et al. |
| 3,743,098 A | * | 7/1973 | Martinez ................ B01D 61/28 210/321.74 |
| 3,957,648 A | | 5/1976 | Roget et al. |
| 4,038,190 A | | 7/1977 | Baudet et al. |
| 4,225,439 A | | 9/1980 | Spranger |
| 4,229,305 A | | 10/1980 | Fecondini et al. |
| 4,597,868 A | | 7/1986 | Watanabe |
| 4,639,353 A | | 1/1987 | Takemura et al. |

(Continued)

FOREIGN PATENT DOCUMENTS

| | | |
|---|---|---|
| CN | 1042082 A | 5/1990 |
| CN | 1308549 A | 8/2001 |

(Continued)

OTHER PUBLICATIONS

European Search Report issued in EP Application No. 10161451, dated Sep. 28, 2010, 5 pages.

(Continued)

*Primary Examiner* — Ariana Zimbouski
(74) *Attorney, Agent, or Firm* — Seager, Tufte & Wickhem LLP

(57) ABSTRACT

A blood processing apparatus includes an optional heat exchanger and a gas exchanger disposed within a housing. In some instances, the gas exchanger can include a screen filter spirally wound into the gas exchanger such that blood passing through the gas exchanger passes through the screen filter and is filtered by the spirally wound screen filter a plurality of times.

20 Claims, 8 Drawing Sheets

(56) References Cited

U.S. PATENT DOCUMENTS

| | | |
|---|---|---|
| 4,707,268 A | 11/1987 | Shah et al. |
| 4,758,341 A | 7/1988 | Banner |
| 4,902,476 A | 2/1990 | Gordon et al. |
| 5,120,501 A | 6/1992 | Mathewson et al. |
| 5,169,530 A | 12/1992 | Schucker et al. |
| 5,192,439 A | 3/1993 | Roth et al. |
| 5,192,499 A | 3/1993 | Sakai et al. |
| 5,270,004 A | 12/1993 | Cosentino et al. |
| 5,316,724 A | 5/1994 | Mathewson et al. |
| 5,338,512 A | 8/1994 | Mathewson et al. |
| 5,514,095 A | 5/1996 | Brightbill et al. |
| 5,578,267 A | 11/1996 | Cosentino et al. |
| 5,651,765 A | 7/1997 | Haworth et al. |
| 5,674,452 A | 10/1997 | Carson et al. |
| 5,733,398 A | 3/1998 | Carson et al. |
| 5,762,868 A | 6/1998 | Leonard |
| 5,762,869 A | 6/1998 | White et al. |
| 5,817,278 A | 10/1998 | Fini et al. |
| 5,817,279 A | 10/1998 | Eilers et al. |
| 5,830,370 A | 11/1998 | Maloney et al. |
| RE36,774 E | 7/2000 | Cosentino et al. |
| 6,105,664 A | 8/2000 | Gillbrand et al. |
| 6,113,782 A | 9/2000 | Leonard |
| 6,241,945 B1 | 6/2001 | Owen |
| 6,454,999 B1 | 9/2002 | Farhangnia et al. |
| 6,459,937 B1 | 10/2002 | Morgan et al. |
| 6,755,894 B2 | 6/2004 | Bikson et al. |
| 6,960,322 B2 | 11/2005 | Stringer et al. |
| 7,431,754 B2 | 10/2008 | Ogihara et al. |
| 7,947,113 B2 | 5/2011 | Ogihara et al. |
| 7,981,121 B2 | 7/2011 | Stegfeldt et al. |
| 8,142,546 B2 | 3/2012 | Ogihara et al. |
| 8,318,092 B2 | 11/2012 | Reggiani et al. |
| 8,388,566 B2 | 3/2013 | Reggiani et al. |
| 8,394,049 B2 | 3/2013 | Reggiani et al. |
| 8,425,838 B2 | 4/2013 | Mizoguchi et al. |
| 8,652,406 B2 | 2/2014 | Reggiani et al. |
| 8,685,319 B2 | 4/2014 | Olson et al. |
| 8,795,220 B2 | 8/2014 | Reggiani et al. |
| 8,865,067 B2 | 10/2014 | Olson et al. |
| 8,911,666 B2 | 12/2014 | Mizoguchi et al. |
| 8,980,176 B2 | 3/2015 | Reggiani et al. |
| 9,162,022 B2 | 10/2015 | Reggiani et al. |
| 9,402,943 B2 | 8/2016 | Reggiani et al. |
| 10,098,994 B2 | 10/2018 | Silvestri et al. |
| 10,159,777 B2 | 12/2018 | Reggiani et al. |
| 10,369,262 B2 | 8/2019 | Reggiani |
| 2001/0033813 A1 | 10/2001 | Filho et al. |
| 2002/0039543 A1 | 4/2002 | Ikeda et al. |
| 2002/0049401 A1 | 4/2002 | Ghelli et al. |
| 2003/0080047 A1 | 5/2003 | Watkins et al. |
| 2003/0111414 A1 | 6/2003 | Baurmeister et al. |
| 2003/0175149 A1 | 9/2003 | Searles et al. |
| 2004/0149645 A1 | 8/2004 | Sunohara et al. |
| 2004/0175292 A1 | 9/2004 | Ghelli et al. |
| 2004/0251011 A1 | 12/2004 | Kudo |
| 2006/0016743 A1* | 1/2006 | Ogihara .............. A61M 1/3627 |
| | | 210/321.89 |
| 2007/0009378 A1 | 1/2007 | Blicke et al. |
| 2007/0107884 A1 | 5/2007 | Sirkar et al. |
| 2007/0166190 A1 | 7/2007 | Ogihara et al. |
| 2007/0231203 A1 | 10/2007 | Mizoguchi et al. |
| 2008/0234623 A1 | 9/2008 | Strauss et al. |
| 2009/0018629 A1 | 1/2009 | Yoshida et al. |
| 2010/0106072 A1 | 4/2010 | Kashefi-Khorasani et al. |
| 2010/0269342 A1 | 10/2010 | Carpenter et al. |
| 2010/0272606 A1 | 10/2010 | Carpenter et al. |
| 2010/0272607 A1 | 10/2010 | Carpenter et al. |
| 2011/0268608 A1 | 11/2011 | Reggiani et al. |
| 2011/0268609 A1 | 11/2011 | Reggiani et al. |
| 2012/0046594 A1 | 2/2012 | Reggiani et al. |
| 2012/0121463 A1 | 5/2012 | Reggiani et al. |
| 2012/0294761 A1 | 11/2012 | Reggiani et al. |
| 2013/0142695 A1 | 6/2013 | Reggiani et al. |
| 2013/0142696 A1 | 6/2013 | Reggiani et al. |
| 2014/0030146 A1 | 1/2014 | Takeuchi |
| 2014/0154137 A1 | 6/2014 | Kashefi Khorasani |
| 2014/0227133 A1 | 8/2014 | Reggiani et al. |
| 2015/0068670 A1 | 3/2015 | Mizoguchi et al. |
| 2016/0325036 A1 | 11/2016 | Silvestri et al. |
| 2016/0354529 A1 | 12/2016 | Reggiani et al. |
| 2017/0072123 A1 | 3/2017 | Reggiani |
| 2017/0319767 A1 | 11/2017 | Zaniboni et al. |
| 2018/0133388 A1 | 5/2018 | Mazzoli et al. |
| 2019/0091395 A1 | 3/2019 | Reggiani et al. |

FOREIGN PATENT DOCUMENTS

| | | |
|---|---|---|
| CN | 2511309 Y | 9/2002 |
| CN | 2772515 Y | 4/2006 |
| CN | 1907508 A | 2/2007 |
| CN | 1914474 A | 2/2007 |
| CN | 201510571 U | 6/2010 |
| CN | 101837151 A | 9/2010 |
| CN | 201978219 U | 9/2011 |
| CN | 103180032 A | 6/2013 |
| CN | 103328019 A | 9/2013 |
| CN | 103547298 A | 1/2014 |
| CN | 106029118 A | 10/2016 |
| DE | 19782098 T1 | 11/1999 |
| DE | 102007010112 A1 | 9/2008 |
| DE | 102010027973 A1 | 10/2011 |
| EP | 0170210 A2 | 2/1986 |
| EP | 0312125 A1 | 4/1989 |
| EP | 0582959 A1 | 2/1994 |
| EP | 0895786 A1 | 2/1999 |
| EP | 1108462 A2 | 6/2001 |
| EP | 1180374 A1 | 2/2002 |
| EP | 0876170 B1 | 10/2003 |
| EP | 1371381 A1 | 12/2003 |
| EP | 1618906 A1 | 1/2006 |
| EP | 1834656 B1 | 5/2010 |
| EP | 2420262 A1 | 2/2012 |
| EP | 2524712 A1 | 11/2012 |
| EP | 2537543 A1 | 12/2012 |
| JP | 44-005526 Y1 | 2/1969 |
| JP | 52-126681 A | 10/1977 |
| JP | 59-147603 A | 8/1984 |
| JP | 60-053156 A | 3/1985 |
| JP | 61-078407 A | 4/1986 |
| JP | 63-139562 A | 6/1988 |
| JP | 63-283709 A | 11/1988 |
| JP | 03-169329 A | 7/1991 |
| JP | 04-002067 B2 | 1/1992 |
| JP | 04-039862 B2 | 6/1992 |
| JP | 0439862 B2 | 6/1992 |
| JP | 05-177117 A | 7/1993 |
| JP | 07-088178 A | 4/1995 |
| JP | 08-168525 A | 7/1996 |
| JP | 11-508476 A | 7/1999 |
| JP | 2000-501954 A | 2/2000 |
| JP | 2000-093510 A | 4/2000 |
| JP | 3228518 B2 | 11/2001 |
| JP | 2002-506692 A | 3/2002 |
| JP | 3284568 B2 | 5/2002 |
| JP | 2002-306592 A | 10/2002 |
| JP | 2003-520617 A | 7/2003 |
| JP | 2003-525736 A | 9/2003 |
| JP | 2004-216143 A | 8/2004 |
| JP | 2006-034466 A | 2/2006 |
| JP | 2007-190218 A | 8/2007 |
| JP | 2007-244880 A | 9/2007 |
| JP | 2007-260151 A | 10/2007 |
| JP | 3992377 B2 | 10/2007 |
| JP | 2007-328114 A | 12/2007 |
| JP | 2009-093659 A | 4/2009 |
| JP | 2011-047269 A | 3/2011 |
| JP | 5020111 B2 | 9/2012 |
| JP | 2012-239885 A | 12/2012 |
| JP | 2013-063121 A | 4/2013 |
| JP | 2015-144857 A | 8/2015 |
| JP | 2017-510340 A | 4/2017 |
| WO | 97/16213 A2 | 5/1997 |
| WO | 97/19714 A1 | 6/1997 |

(56) References Cited

FOREIGN PATENT DOCUMENTS

| WO | 97/33636 | A1 | 9/1997 |
|---|---|---|---|
| WO | 99/47189 | A1 | 9/1999 |
| WO | 99/58171 | A2 | 11/1999 |
| WO | 2010/124087 | A1 | 10/2010 |
| WO | 2012/066439 | A1 | 5/2012 |
| WO | 2012/133372 | A1 | 10/2012 |
| WO | 2015/104725 | A1 | 7/2015 |
| WO | 2015/107486 | A2 | 7/2015 |
| WO | 2015/128886 | A1 | 9/2015 |

OTHER PUBLICATIONS

European Search Report issued in EP Application No. 10173436, dated Feb. 14, 2011, 7 pages.
European Search Report issued in EP Application No. 10186550, dated Jan. 27, 2011, 7 pages.
European Search Report issued in EP Application No. 10191140, dated Nov. 30, 2011, 8 pages.
European Search Report issued in EP Application No. 12187501, dated Nov. 20, 2013, 6 pages.
European Search Report issued in EP Application No. 13161841, dated Jun. 11, 2013, 6 pages.
International Search Report and Written Opinion issued in PCT/IB2012/052424, dated Oct. 24, 2012, 17 pages.
International Search Report and Written Opinion issued in PCT/IB2014/065987, dated Jul. 16, 2015, 10 pages.
International Search Report and Written Opinion issued in PCT/IB2015/053493, dated Jan. 18, 2016, 13 pages.
International Search Report and Written Opinion issued in PCT/IT2014/000005, dated Sep. 26, 2014, 9 pages.
International Search Report and Written Opinion issued in PCT/IT2014/000058, dated Dec. 8, 2014, 14 pages.
International Search Report and Written Opinion received for PCT Patent Application No. PCT/IT2014/000005, dated Sep. 26, 2014, 8 pages.
International Search Report issued in PCT/IB2011/054725, dated Feb. 9, 2012, 12 pages.
Italian Search Report issued in IT Application No. IT MO20140010, completed Sep. 23, 2014, 7 pages.

* cited by examiner

SYSTEM FOR PROVIDING AN INTEGRATED ARTERIAL FILTER INTO AN OXYGENATOR, MINIMIZING ADDED PRIMING VOLUME

CROSS-REFERENCE TO RELATED APPLICATION

This application is a continuation of U.S. patent application Ser. No. 15/121,768, filed Aug. 25, 2016, which is a national stage application of PCT/IT2014/000058, internationally filed Feb. 28, 2014, both of which are incorporated by reference in their entirety.

TECHNICAL FIELD

The disclosure pertains generally to arterial filters used in blood perfusion systems and more particularly to arterial filters that are integrated into an oxygenator.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. In some cases, blood is drained inside a reservoir that filters out solid and gaseous emboli, while in other cases such as in mini bypass applications, a relatively small volume venous bubble trap can be used instead of a large volume venous reservoir. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral, or other artery.

Often, an arterial filter is added to the extracorporeal circuit, after the oxygenator, as a last barrier before the patient, so as to block any solid or gaseous emboli and prevent any such emboli from entering into the aorta of the patient. Recently, arterial filters integrated in the oxygenator have been developed, allowing the reduction of the priming volume of the circuit and decreasing the global haemodilution of the patient. In some cases, excessive haemodilution is one of the major post-operative causes of patient morbidity, and should be avoided.

SUMMARY

In some embodiments, the disclosure is directed to a filter assembly for use in a blood processing apparatus. The filter assembly includes a filter mesh screen having an average pore size of about 20 microns to about 150 microns and a plurality of hollow gas exchange fibers secured to the filter mesh screen. The filter mesh screen is spirally wound to form a filter assembly that is useable as a gas exchanger. Blood flowing between the plurality of hollow gas exchange fibers is filtered by the filter mesh screen.

In some embodiments, the disclosure is directed to a blood processing apparatus that includes an apparatus housing having a blood inlet and a blood outlet, the blood inlet extending into an interior of the apparatus housing. In some embodiments, a heat exchanger is in fluid communication with the blood inlet and is disposed about the blood inlet. A gas exchanger is disposed about the heat exchanger such that an inner surface of the gas exchanger is positioned to receive blood exiting an outer surface of the heat exchanger. In some embodiments, there is no heat exchanger, and the gas exchanger is disposed about the blood inlet. A screen filter is spirally wound through the gas exchanger such that blood passing through the gas exchanger passes through the screen filter and is filtered by the spirally wound screen filter a plurality of times.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
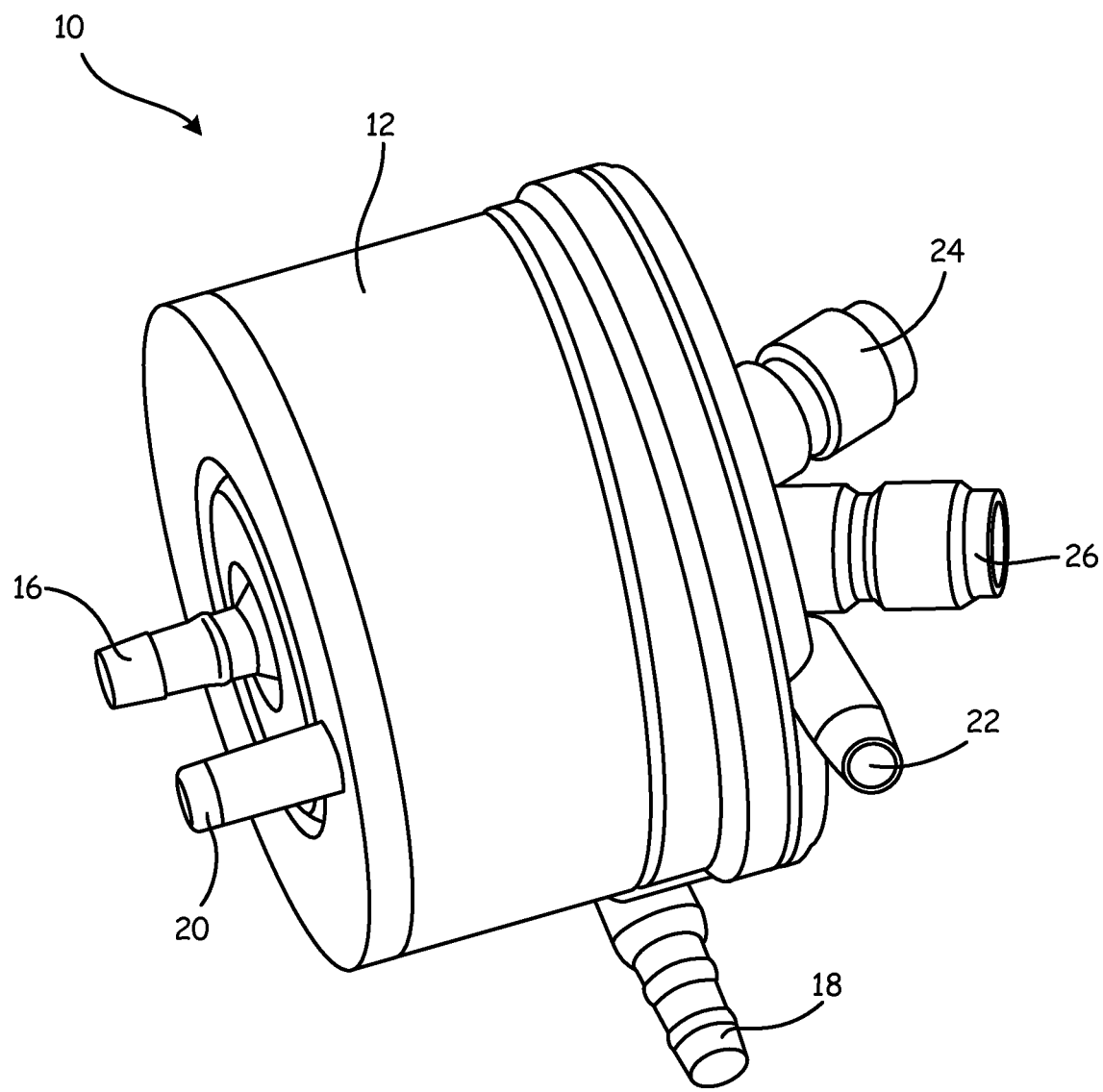
FIG. 1 is a schematic illustration of a blood processing apparatus including an integrated arterial filter in accordance with embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The disclosure pertains to a blood processing apparatus that combines, in a single structure, an optional heat exchanger, a gas exchanger or oxygenator and an arterial filter. In some embodiments, the term oxygenator with integrated arterial filter may be used to refer to a structure that combines an optional heat exchanger, a gas exchanger and an arterial filter in a unitary device. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

In some embodiments, by combining the arterial filter with the oxygenator, the tubing set used to create the extracorporeal blood circuit may be reduced in complexity or number of parts and thus may simplify the extracorporeal blood circuit. In some embodiments, this will reduce the priming volume of the extracorporeal blood circuit. To illustrate, for a particular neonatal-sized oxygenator utilizing a separate arterial filter, the priming volume is about 47 milliliters (ml). A similar neonatal-sized oxygenator made in accordance with the disclosure, with an arterial filter integrated within the oxygenator, has a priming volume of about 35 ml. This represents a substantial reduction in priming volume of about 25 percent.

FIG. 1 is a schematic illustration of a blood processing apparatus or oxygenator 10. While the internal components are not visible in this illustration, the oxygenator 10 may include one or more of a heat exchanger, a gas exchanger and an arterial filter. According to some embodiments, each of the heat exchanger, gas exchanger and arterial filter are integrated into a single structure disposed within a device compartment or housing 12. In some embodiments, as will be discussed, the gas exchanger may include an arterial filter that is integrated into the gas exchanger itself.

According to various embodiments the heat exchanger (if present), the gas exchanger, and the device housing 12 may have a cross-section shaped generally as a circle. Each of the heat exchanger, the gas exchanger and the device housing 12 may have generally the same sectional shape or each may have a different sectional shape.

In some embodiments, a blood inlet 16 extends into the device housing 12. A blood outlet 18 exits the device housing 12. As noted, in some embodiments the oxygenator 10 includes a gas exchanger and thus may include a gas inlet 20 and a gas outlet 22. In some embodiments, the oxygenator 10 includes a heat exchanger and thus may include a heating fluid inlet 24 and a heating fluid outlet 26. While not illustrated, in some embodiments it is contemplated that the oxygenator 10 may include one or more purge ports for eliminating air bubbles entrained within the blood. It is to be understood that the positions of the inlets and outlets are merely illustrative, as other arrangements and configurations are contemplated.

Figure 1A:
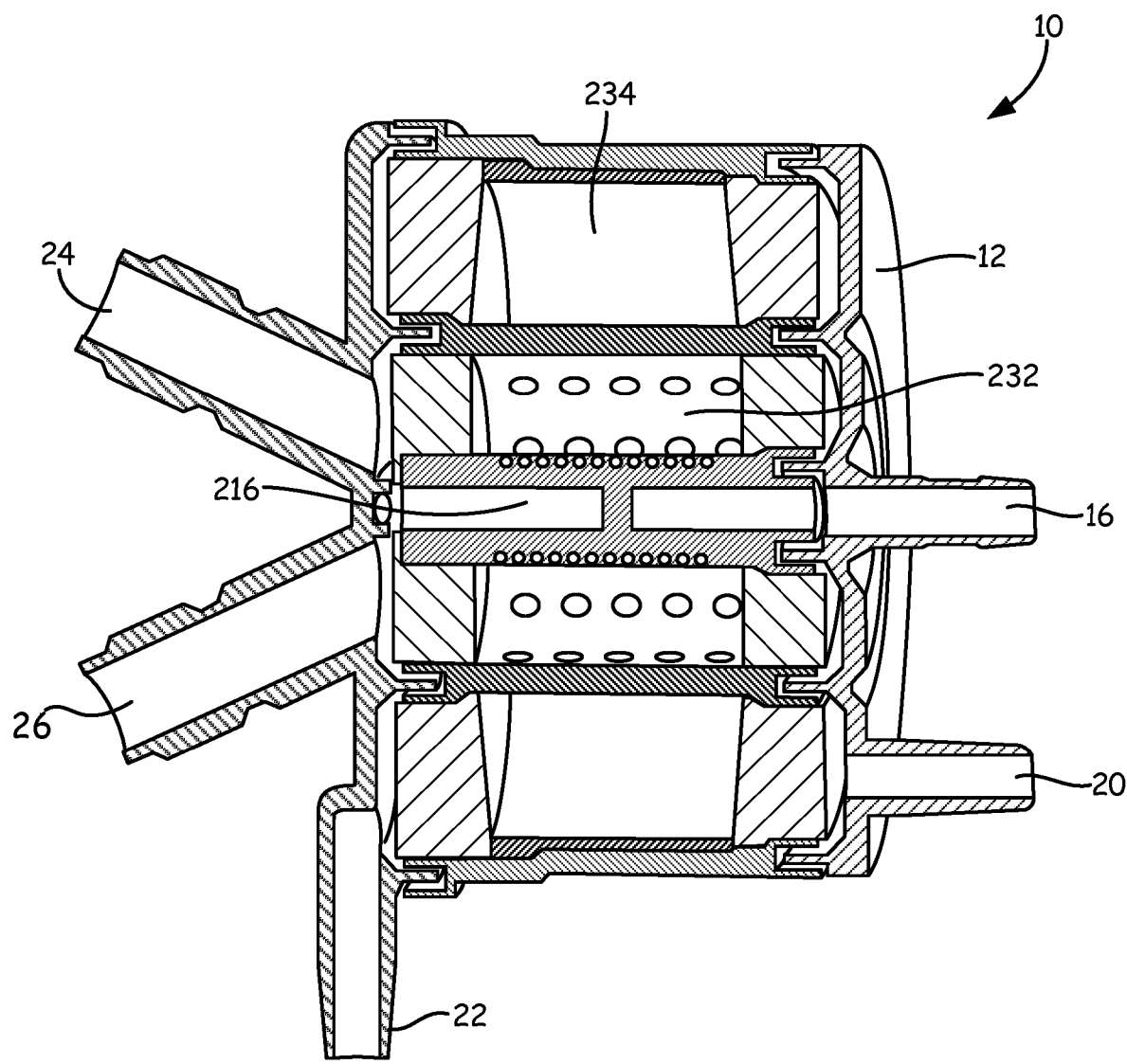
FIG. 1A is a schematic cross-sectional illustration of the blood processing apparatus of FIG. 1.

FIG. 1A is a cross-sectional view of the oxygenator 10, illustrating the relative position of a heat exchanger 232 and a gas exchanger 234. Blood enters the oxygenator 10 via the blood inlet 16 and passes from the blood inlet 16 into a heat exchanger core 216 and then through the heat exchanger 232. Heating and/or cooling fluid may enter through the heating fluid inlet 24, pass through the hollow fibers (not illustrated) forming the heat exchanger 232, and exit the oxygenator 10 via the heating fluid outlet 26. Blood entering the heat exchanger 232 flows around and over the aforementioned hollow fibers and exits the heat exchanger 232. Blood exiting the heat exchanger 232 flows into the gas exchanger 234. Oxygen enters the oxygenator 10 via the gas inlet 20, flows through hollow fibers (not illustrated in this view) within the gas exchanger 234, and exits through the gas outlet 22, carrying carbon dioxide and other gases that diffuse through and out of the hollow fibers. The heated and oxygenated blood can then exit through the blood outlet 18 (FIG. 1).

Figure 1B:
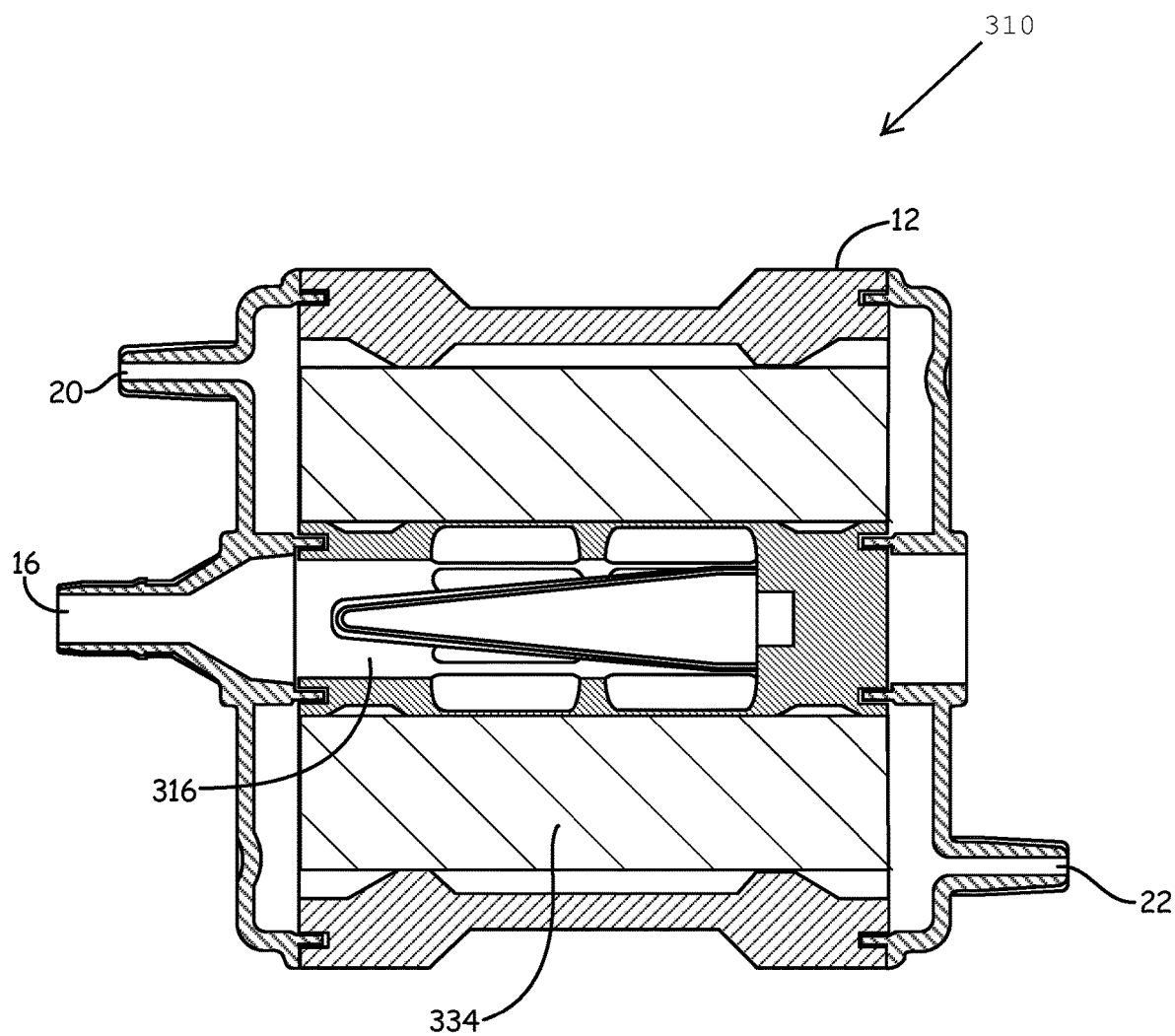
FIG. 1B is an alternate schematic cross-sectional illustration of the blood processing apparatus of FIG. 1.

FIG. 1B is an alternate cross-sectional view of an oxygenator 310, illustrating a gas exchanger 334. The oxygenator 310 does not include a heat exchanger. Blood enters the oxygenator 310 via the blood inlet 16 and passes from the blood inlet 16 into a core 316 and then through the gas exchanger 334. Oxygen enters the oxygenator 310 via the gas inlet 20, flows through hollow fibers (not illustrated in this view) within the gas exchanger 334, and exits through the gas outlet 22, carrying carbon dioxide and other gases that diffuse through and out of the hollow fibers. The heated and oxygenated blood can then exit through the blood outlet 18 (FIG. 1).

In some embodiments, as will be discussed subsequently, the gas exchanger 234 (FIG. 1A) and the gas exchanger 334 (FIG. 1B) incorporate a filtration mechanism that is wound or otherwise disposed within the gas exchanger 234, 334.

Figure 2:
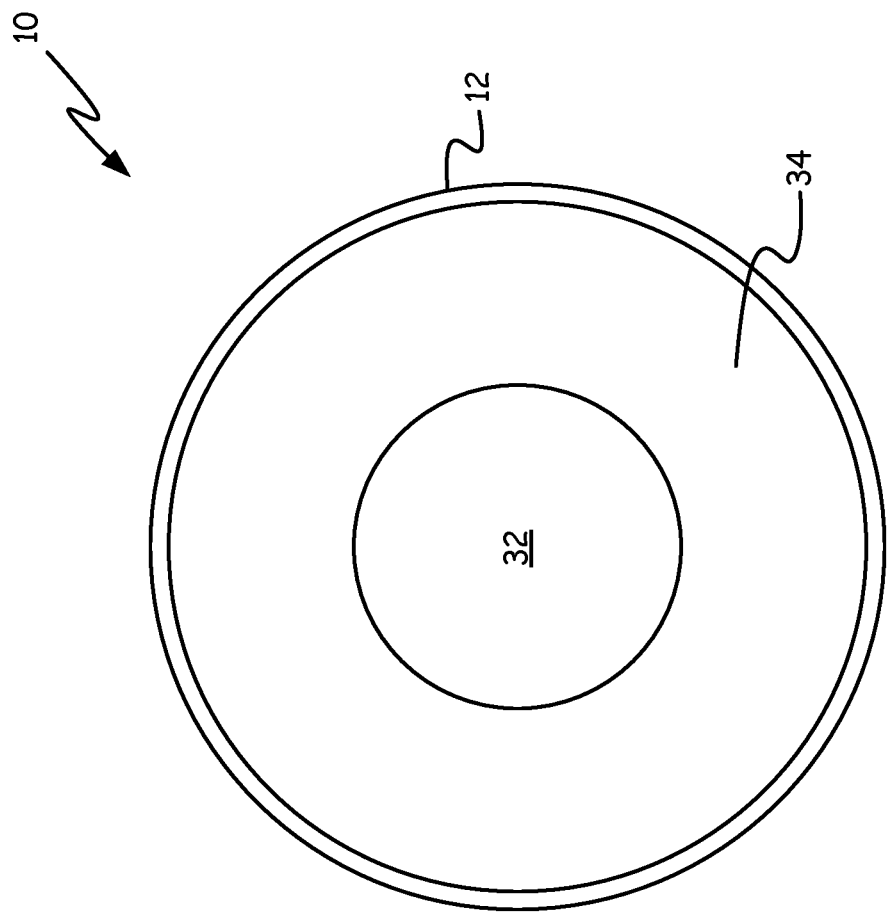
FIG. 2 is a schematic cross-sectional illustration of the blood processing apparatus of FIG. 1.

FIG. 2 is a cross-sectional view of the oxygenator 10, illustrating the relative arrangement of a heat exchanger 32 and a gas exchanger 34. While FIG. 2 illustrates the oxygenator 10 as including the heat exchanger 32, it will be appreciated that in some embodiments the heat exchanger 32 may be excluded. If there is no heat exchanger 32, a cylindrical core may be provided in its place to provide a support for the gas exchanger 34. In this illustration, other internal components such as the inlets and outlets are not shown, for simplicities sake. In some embodiments, the heat exchanger 32 includes a number of hollow fibers through which a heating fluid such as water can flow. The blood may flow around and past the hollow fibers and thus be suitably heated. In some embodiments, the hollow fibers may be polymeric. The hollow fibers are too small to be represented in the drawing. In some cases, metallic fibers may be used within the heat exchanger 32. According to other embodiments, the heat exchanger 32 includes a metal bellows or other structure comprising a substantial surface area (e.g., fins) for facilitating heat transfer with the blood.

In some embodiments the gas exchanger 34 may include a number of hollow fibers through which a gas such as oxygen may flow. The blood may flow around and past the hollow fibers. Due to concentration gradients, oxygen may diffuse through the hollow fibers into the blood while carbon dioxide may diffuse into the hollow fibers and out of the blood. The hollow fibers are too small to be represented in this drawing.

Figure 3:
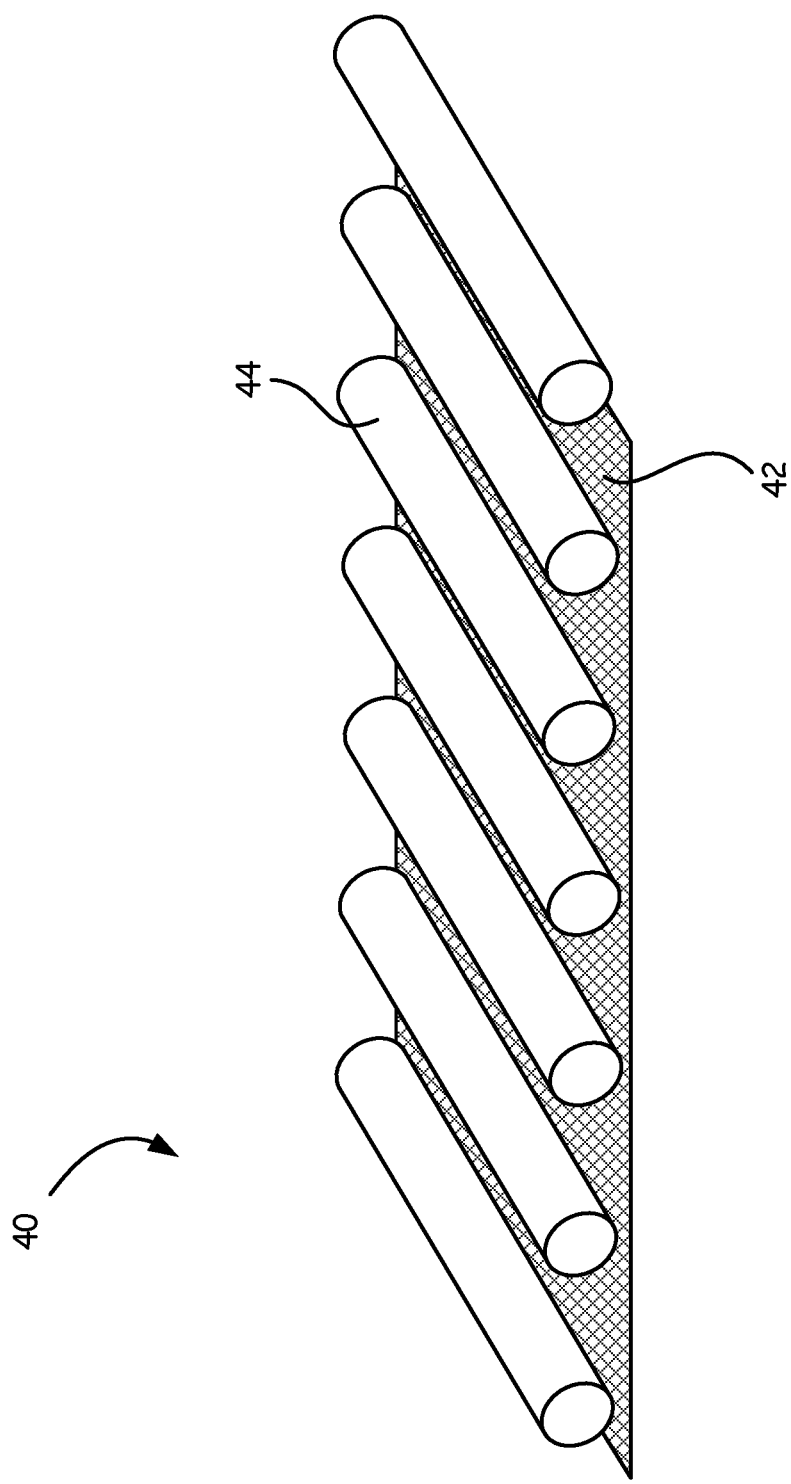
FIG. 3 is a schematic illustration of a composite assembly used to form the blood processing apparatus of FIG. 1.

In some embodiments, the gas exchanger 34 (FIG. 2), 234 (FIG. 1A) and 334 (FIG. 1B) includes an arterial filter that is integrated into the gas exchanger 34, 234, 334. FIG. 3 is a schematic illustration of a composite filter screen assembly 40 that includes a filter screen 42 and a plurality of hollow fibers 44. The schematic illustration is only one of the possibilities for coupling in an assembly a filter mean 42 with a gas exchange fiber mat. In some embodiments, the filter screen 42 may extend along an entire longitudinal length of the assembly. In other embodiments, the filter screen 42 extends longitudinally along only a portion of the longitudinal length of the assembly. In some exemplary embodiments, the screen 42 extends from about 20 to about 80 percent along the longitudinal length of the assembly.

In this illustration, the size of the hollow fibers 44 is blown up out of scale to better illustrate the hollow fibers 44. The filter screen 42, in various embodiments, is a polymeric filter screen having an average pore size, defined as the average distance between adjacent elements, that ranges from about 20 microns to about 150 microns. In various embodiments, the average pore size of the filter screen is from about 60 microns to about 125 microns. In some embodiments, the filter screen 42 can be made from a polypropylene or polyester, although other suitable materials may also be used. In some cases, the filter screen 42, the gas exchange hollow fiber 44 or the whole oxygenator with integrated arterial filter may be coated with a biocompatible material.

The hollow fibers 44 may be polymeric. In some embodiments the hollow fibers are hollow fibers formed from microporous polypropylene or PMP (polymethyl propylene), although other suitable materials may also be used. In some embodiments, the hollow fibers 44 may have an average outer diameter that ranges from about 100 microns to about 1000 microns, and can have an average length corresponding to that of the gas exchanger itself.

Figure 4:
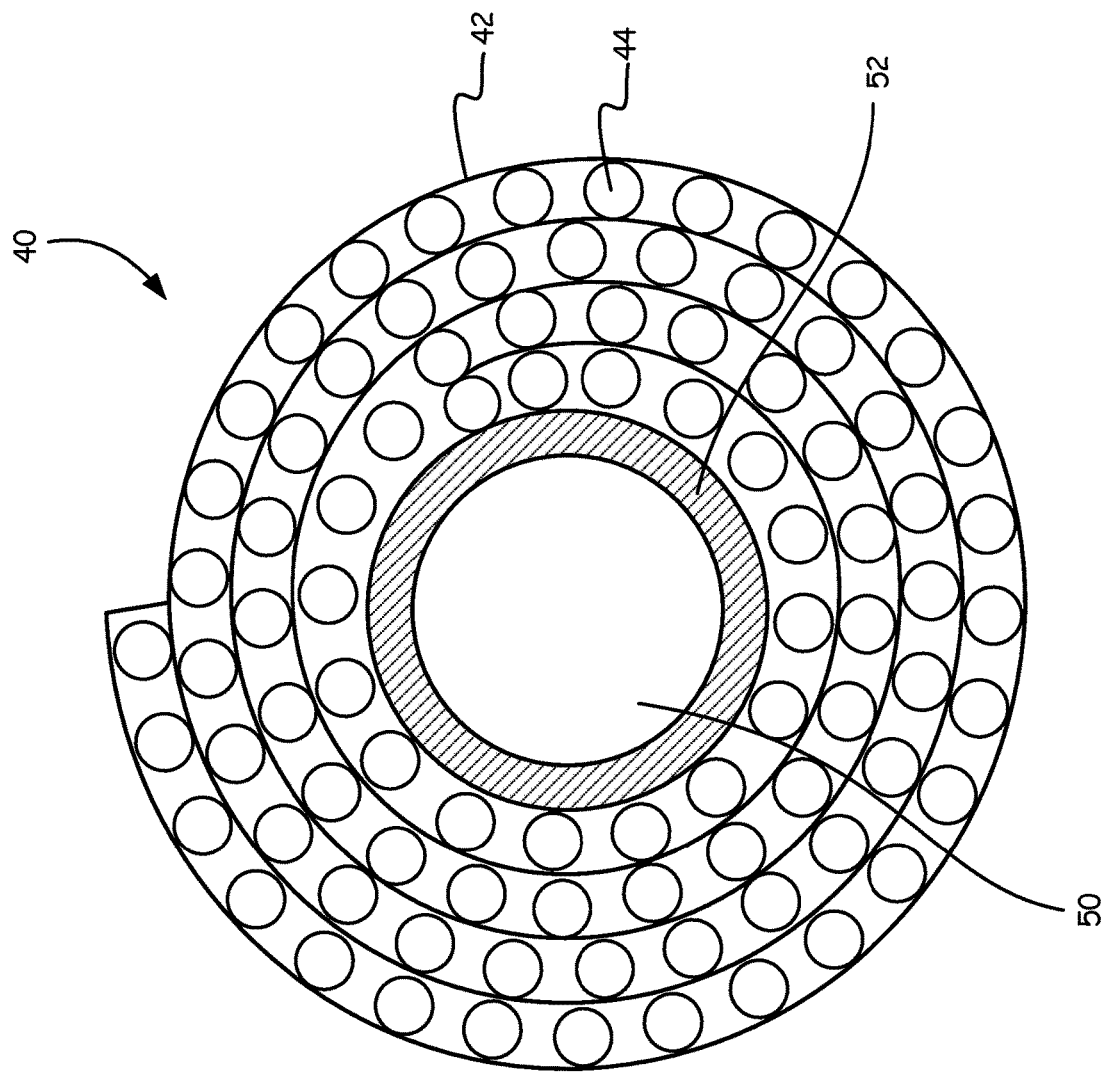
FIG. 4 is a schematic illustration of a portion of the blood processing apparatus of FIG. 1.
Figure 5:
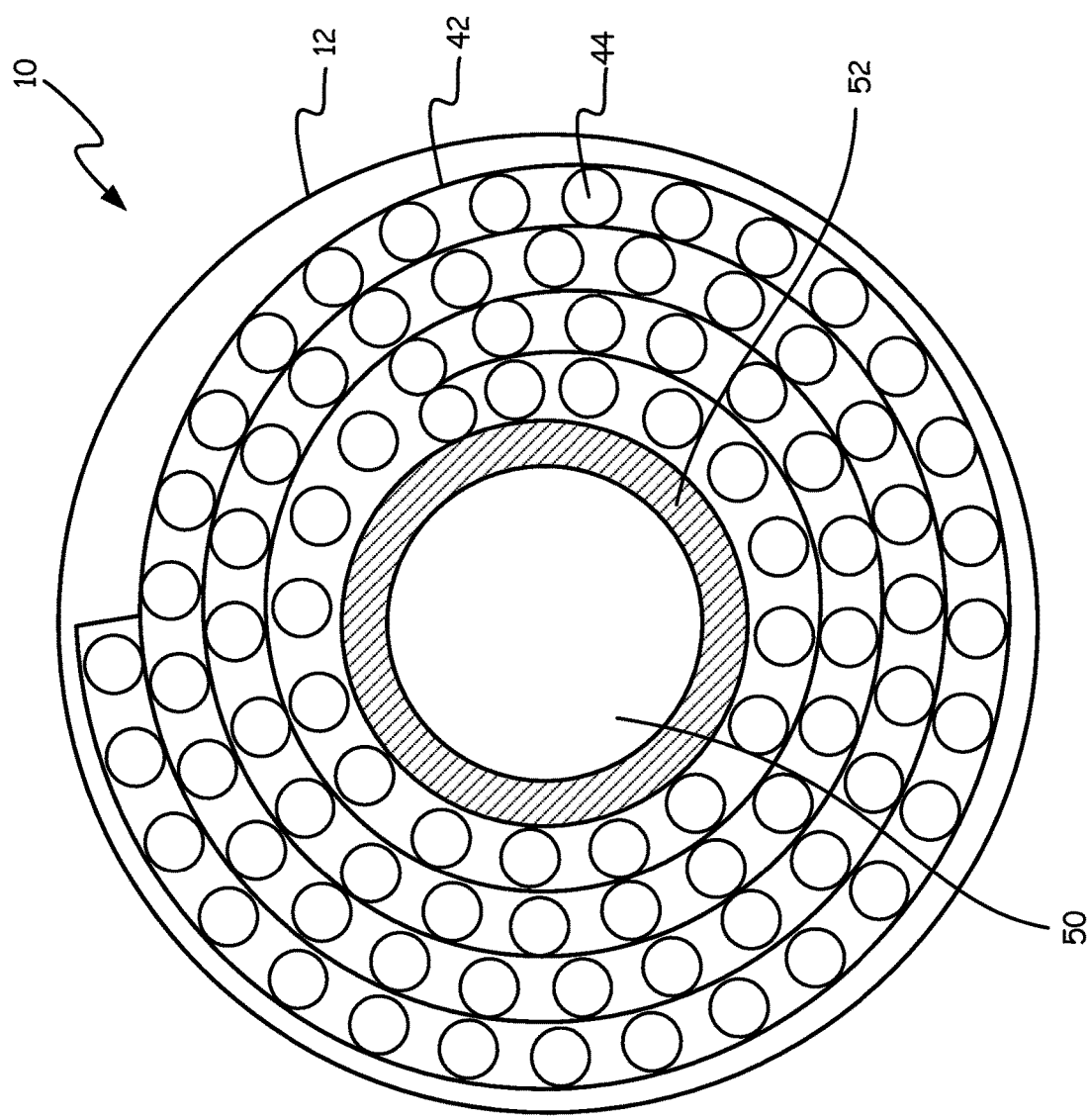
FIG. 5 is a schematic illustration of a portion of the blood processing apparatus of FIG. 1.

FIG. 4 shows the composite assembly 40 rolled over an oxygenator core 52. In some embodiments, the composite assembly 40 can be rolled directly over a heat exchanger. FIG. 5 is similar but also illustrates the housing 12. Optionally, the composite assembly 40 may be rolled over itself in a spiral fashion. In either case, it can be seen that the filter screen 42 is disposed within the gas exchanger 34 in a spiral fashion. As schematically illustrated, the composite assembly 40 is sized such that the composite assembly 40 forms about four complete layers about the oxygenator core 52. It will be appreciated that this is for simplifying the image, as in some embodiments, the composite assembly 40 may be sized to permit about 5 to about 100 complete layers. As blood exits the heat exchanger 32, it will be appreciated that as blood moves radially outwardly, the blood will pass through the filter screen 42 a plurality of times.

It can be seen that the oxygenator core 52 defines a volume 50 that corresponds to the location of the heat exchanger 32. The oxygenator core 52 can be formed of any suitable material, such as any suitable polymeric material, and can have an outer diameter that is in the range of about 10 to about 200 millimeters (mm) and an inner diameter that is in the range of about 5 to about 5-100 mm. In some embodiments, relative dimensions will depend on the patient size and the choice of inner core diameter. While not illustrated in this view, the oxygenator core 52 may include one or more apertures that permit blood to flow from the heat exchanger 32 into the gas exchanger 34. In some embodiments, the oxygenator core 52 may be absent, and thus potting may be used to separate water and gas compartments within the device 10. As discussed above, in some embodiments there is no heat exchanger, and thus the oxygenator core 52 would be empty.

Figure 6:
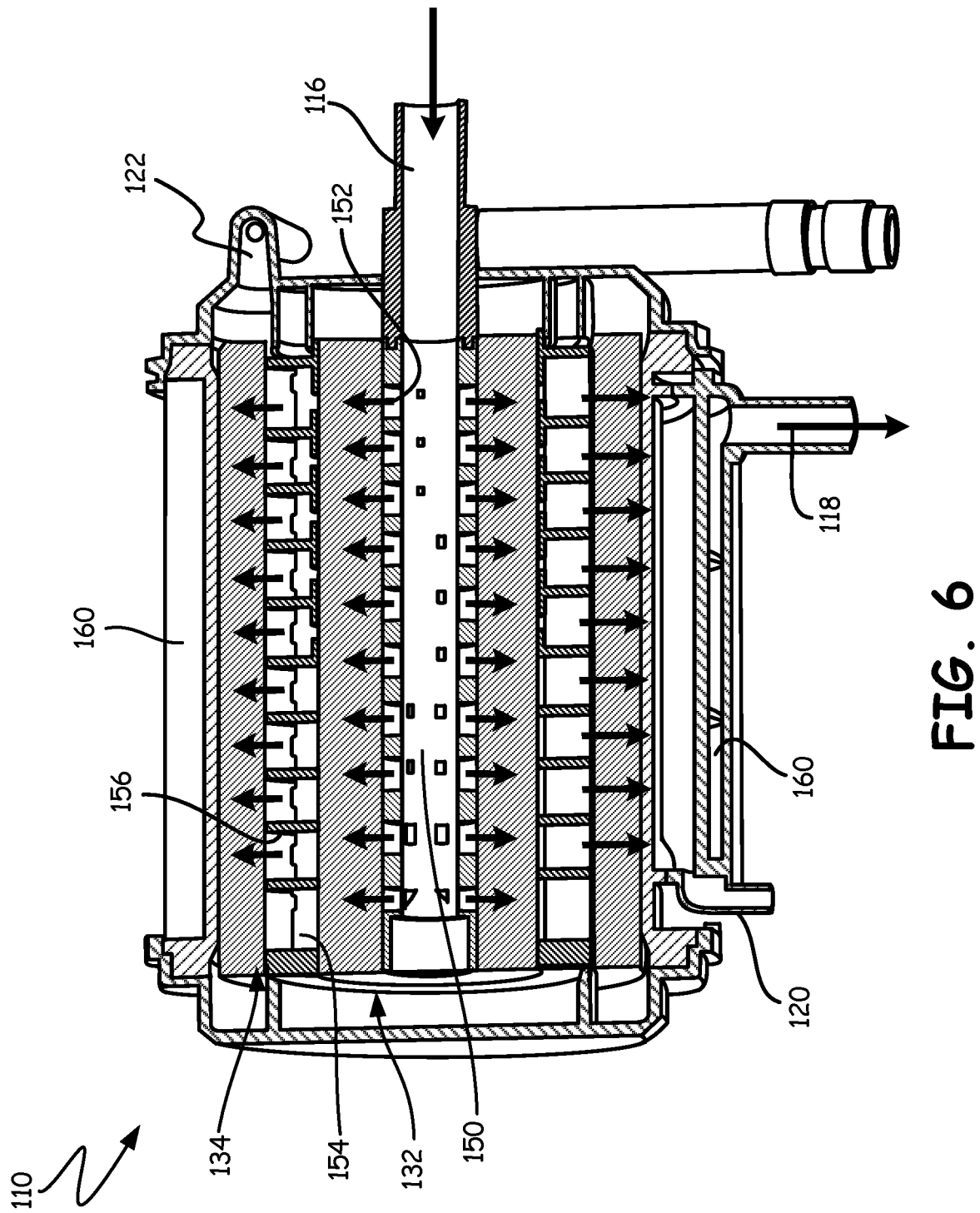
FIG. 6 is a schematic illustration of a blood processing apparatus including an integrated arterial filter in accordance with embodiments of the disclosure.

FIG. 6 provides a longitudinal cross-sectional view of a blood processing apparatus 110. The blood processing apparatus 110 includes a blood inlet 116 and a blood outlet 118. Blood entering via the blood inlet 116 passes into a central core 150. In some embodiments, the central core 150 may include a plurality of apertures 152 that permit the blood to exit the central core 150 and move in a radially outward direction. The blood passes through the hollow fibers (not labeled) within a heat exchanger 132. A shell 154 surrounds and defines the heat exchanger 132. In some embodiments, the shell 154 includes a plurality of apertures 156 that permit blood to exit the heat exchanger 132 and flow through the gas exchanger 134 in a radially outward direction. In some embodiments, the blood exiting the gas exchanger 134 collects in an annular collection space 160 before exiting through the blood outlet 118.

Example

To illustrate the advantages in priming volume achieved by incorporating the arterial filter within the gas exchanger, consider the following example. A neonatal oxygenator D100 available from Sorin combined with a neonatal arterial filter D130 available from Sorin has a total priming volume of 47 ml. In comparison, a D100 oxygenator modified to include the inventive arterial filter incorporated within the gas exchanger has a total priming volume of 35 ml. This represents a 25% reduction. The particular dimensions are given in the Table below:

|  | D100 + D130 | Modified D100 |
| --- | --- | --- |
| core diameter | 5.1 cm | 5.1 cm |
| external case diameter | 5.87 cm | 6.15 cm |
| internal oxy void volume | 21.9 cm$^3$ | 30.5 cm$^3$ |
| fiber volume | 11 cm$^3$ | 11 cm$^3$ |
| filter screen volume | 0 cm$^3$ | 4.6 cm$^3$ |
| oxy priming volume | 10.9 cm$^3$ | 14.9 cm$^3$ |
| HE + connectors priming | 20.1 cm$^3$ | 20.1 cm$^3$ |
| total oxy priming | 31 cm$^3$ | 35 cm$^3$ |
| external arterial filter priming | 16 cm$^3$ | 0 cm$^3$ |
| Total priming | 47 cm$^3$ | 35 cm$^3$ |

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A blood processing apparatus comprising:
an apparatus housing having a blood inlet and a blood outlet, the blood inlet extending into an interior of the apparatus housing;
a core in fluid communication with the blood inlet and disposed about the blood inlet;
a gas exchanger disposed about the core such that an inner surface of the gas exchanger is positioned to receive blood exiting an outer surface of the core; and
a screen filter spirally wound through the gas exchanger such that blood passing through the gas exchanger passes through the spirally wound screen filter a plurality of times to filter the blood.

2. The blood processing apparatus of claim 1, wherein the core comprises a heat exchanger core, and there is a heat exchanger disposed within the heat exchanger core.

3. The blood processing apparatus of claim 1, wherein the core comprises a support for the gas exchanger.

4. The blood processing apparatus of claim 2, wherein the screen filter comprises a screen mesh and wherein a plurality of hollow gas exchange fibers are secured to the screen mesh to form a composite assembly, the composite assembly rolled over itself, about the heat exchanger, to form the gas exchanger.

5. The blood processing apparatus of claim 4, wherein at least some of the hollow gas exchange fibers have an outer diameter ranging from about 100 microns to about 1000 microns.

6. The blood processing apparatus of claim 1, further comprising an annular space being defined between an outer surface of the screen filter and an interior surface of the apparatus housing such that blood exiting the outer surface of the gas exchanger can collect in the annular space, the annular space in fluid communication with the blood outlet.

7. The blood processing apparatus of claim 1, wherein the gas exchanger is configured to permit gas to flow therethrough in order to add oxygen and remove carbon dioxide from the blood passing through the gas exchanger.

8. A blood processing apparatus comprising:
an apparatus housing having a blood inlet and a blood outlet, the blood inlet extending into an interior of the apparatus housing;
a heat exchanger in fluid communication with the blood inlet and disposed about the blood inlet;
a gas exchanger disposed about the heat exchanger such that an inner surface of the gas exchanger is positioned to receive blood exiting an outer surface of the heat exchanger; and
a screen filter spirally wound through the gas exchanger such that blood passing through the gas exchanger passes through the screen filter and is filtered by the spirally wound screen filter a plurality of times;
wherein a plurality of hollow gas exchange fibers is secured to the screen filter to form a composite assembly, the composite assembly rolled being over itself, about the heat exchanger, to form the gas exchanger.

9. The blood processing apparatus of claim 8, wherein at least some of the hollow gas exchange fibers have an outer diameter ranging from about 100 microns to about 1000 microns.

10. The blood processing apparatus of claim 8, wherein the screen filter includes a screen mesh having an average pore size of about 20 microns to about 150 microns.

11. The blood processing apparatus of claim 8, wherein the screen filter is formed from polypropylene or polyester.

12. The blood processing apparatus of claim 8, wherein at least some of the plurality of hollow gas exchange fibers are formed of polypropylene or polymethyl propylene.

13. The blood processing apparatus of claim 8, wherein the plurality of hollow gas exchange fibers is arranged in a mat structure made of two layers of hollow gas exchange fibers, each layer having hollow gas exchange fibers angled and arranged in a criss-cross configuration.

14. The blood processing apparatus of claim 4, wherein the screen mesh has an average pore size of about 20 microns to about 150 microns.

15. The blood processing apparatus of claim 4, wherein the screen mesh is formed from polypropylene or polyester.

16. The blood processing apparatus of claim 4, wherein at least some of the plurality of hollow gas exchange fibers are formed of polypropylene or polymethyl propylene.

17. The blood processing apparatus of claim 4, wherein the plurality of hollow gas exchange fibers is arranged in a mat structure made of two layers of hollow gas exchange fibers, each layer having hollow gas exchange fibers angled and arranged in a criss-cross configuration.

18. A blood processing apparatus comprising:
an apparatus housing having a blood inlet and a blood outlet, the blood inlet extending into an interior of the apparatus housing;
a core in fluid communication with the blood inlet and disposed about the blood inlet;
a gas exchanger disposed about the core such that an inner surface of the gas exchanger is positioned to receive blood exiting an outer surface of the core; and
a screen filter spirally wound through the gas exchanger such that blood passing through the gas exchanger passes through the screen filter and is filtered by the spirally wound screen filter a plurality of times;
wherein the screen filter comprises a screen mesh and wherein a plurality of hollow gas exchange fibers is secured to the screen mesh to form a composite assembly, the composite assembly being rolled over itself, about the core, to form the gas exchanger.

19. The blood processing apparatus of claim 18, wherein the screen mesh has an average pore size of about 60 microns to about 125 microns.

20. The blood processing apparatus of claim 18, wherein the composite assembly forms at least four complete layers surrounding the core.

* * * * *